US012606511B2

(12) United States Patent
Shiflett et al.

(10) Patent No.: US 12,606,511 B2
(45) Date of Patent: Apr. 21, 2026

(54) PROCESSES FOR THE ACYLATION OF AN AROMATIC COMPOUND

(71) Applicant: University of Kansas, Lawrence, KS (US)

(72) Inventors: Mark Brandon Shiflett, Lawrence, KS (US); Rajkumar Kore, Lawrence, KS (US); Aaron M. Scurto, Oskaloosa, KS (US)

(73) Assignee: University of Kansas, Lawrence, KS (US)

( * ) Notice: Subject to any disclaimer, the term of this patent is extended or adjusted under 35 U.S.C. 154(b) by 557 days.

(21) Appl. No.: 18/042,559

(22) PCT Filed: Aug. 20, 2021

(86) PCT No.: PCT/US2021/046882
§ 371 (c)(1),
(2) Date: Feb. 22, 2023

(87) PCT Pub. No.: WO2022/046552
PCT Pub. Date: Mar. 3, 2022

(65) Prior Publication Data

US 2023/0373893 A1 Nov. 23, 2023

Related U.S. Application Data

(60) Provisional application No. 63/069,332, filed on Aug. 24, 2020.

(51) Int. Cl.
*C07C 45/46* (2006.01)
*C07D 233/58* (2006.01)

(52) U.S. Cl.
CPC ............ *C07C 45/46* (2013.01); *C07D 233/58* (2013.01)

(58) Field of Classification Search
CPC ...................................................... C07C 45/46
See application file for complete search history.

(56) References Cited

U.S. PATENT DOCUMENTS

| | | | |
|---|---|---|---|
| 5,824,832 | A | 10/1998 | Sherif et al. |
| 6,348,631 | B1 | 2/2002 | Desmurs et al. |
| 7,314,962 | B2 | 1/2008 | Harmer et al. |
| 7,683,209 | B2 | 3/2010 | Harmer et al. |
| 8,283,492 | B2 | 10/2012 | Harmer et al. |
| 8,524,965 | B2 | 9/2013 | Campbell et al. |
| 10,246,395 | B2 | 4/2019 | Rogers et al. |
| 10,301,233 | B2 | 5/2019 | Timken et al. |
| 2007/0100184 | A1 | 5/2007 | Harmer et al. |
| 2010/0331599 | A1 | 12/2010 | Subramaniam et al. |
| 2015/0273460 | A1 | 10/2015 | Buchbinder et al. |
| 2016/0009612 | A1 | 1/2016 | Riley et al. |
| 2016/0060277 | A1 | 3/2016 | Aduri et al. |
| 2016/0168054 | A1 | 6/2016 | Kalnes et al. |
| 2018/0170847 | A1 | 6/2018 | Alabama |
| 2023/0322646 | A1 | 10/2023 | Shiflett et al. |
| 2023/0322662 | A1 | 10/2023 | Shiflett et al. |
| 2023/0322663 | A1 | 10/2023 | Shiflett et al. |

FOREIGN PATENT DOCUMENTS

| | | | | |
|---|---|---|---|---|
| CN | 1785941 | A | | 6/2006 |
| CN | 105209419 | A | | 12/2015 |
| CN | 106010636 | A | | 10/2016 |
| CN | 106944132 | A | | 7/2017 |
| CN | 108525703 | A | | 9/2018 |
| CN | 109824491 | A | * | 5/2019 |
| DE | 11 2004 001 729 | T5 | | 10/2006 |
| IN | 201621019184 | A | | 12/2017 |
| WO | WO 2007/044270 | A1 | | 4/2007 |
| WO | 2009032962 | A2 | | 3/2009 |
| WO | 2016161202 | A1 | | 10/2016 |
| WO | WO 2018/104875 | A1 | | 6/2018 |
| WO | 2014181345 | A2 | | 11/2024 |

OTHER PUBLICATIONS

CN109824491A, machine translation, May 3, 2019, pp. 1-20 (Year: 2019).*

Zhang, et al.,"Isobutane/2-butene alkylation catalyzed by chloroaluminate ionic liquids in the presence of aromatic additives," Journal of Catalysis, Jun. 12, 2007, pp. 261-268, vol. 249.

E. Campaigne et al., "Simultaneous Vicinal Dichlorination," J. Am. Chem. Soc. (Jan. 1950), 72, 1; 629-630.

Peng Cui et al., "Ionic liquid enhanced alkylation of iso-butane and 1-butene," *Catalysis Today* (2013), 200; pp. 30-35.

Wikipedia, "Lewis acids and bases." May 22, 2019; retrieved from https://en.wikipedia.org/w/index.php?title=Lewis_acids_and_bases&oldid=898242465;pp. 1-10.

Congzhen Qiao et al., "Benzene alkylation with long chain olefins catalyzed by ionic liquids: a review," Front. Chem. Eng. China 2008, 2(3): 346-352. DOI 10.1007/x11705-008-0045-9.

(Continued)

*Primary Examiner* — Medhanit W Bahta

(74) *Attorney, Agent, or Firm* — Bell & Manning, LLC

(57) ABSTRACT

Processes for acylating an aromatic compound are provided. In embodiments, such a process comprises combining an aromatic compound, an acylating agent, and a catalyst composition under conditions to induce acylation of the aromatic compound with the acylating agent, the catalyst composition comprising components selected from the group consisting of a sulfonic acid of formula $R—SO_3H$, wherein R is a linear alkyl group substituted with one or more halogen atoms; an ionic liquid and an acid; an acid and a base capable of forming an ionic liquid with the acid; an ionic liquid, an acid, and an aromatic; and an acid, a base capable of forming an ionic liquid with the acid, and an aromatic. The ionic liquid does not comprise a metal halide and the catalyst composition is free of a metal halide and the aromatic, if present in the catalyst composition, is not the aromatic compound being acylated.

20 Claims, 6 Drawing Sheets

(56) References Cited

OTHER PUBLICATIONS

Yibo He et al., "Synthesis of efficient SBA-15 immobilized ionic liquid catalyst and its performance for Friedel-Crafts reaction," *Catalysis Today* 276 (2016) 112-120.

Rajkumar Kore et al., ZSM-5 Zeolite Nanosheets with Improved Catalytic Activity Synthesized Using a New Class of Structure-Directing Agents, *Chemistry A European Journal* 2014, 20, 1-12. DOI: 10.1002/chem.201402665.

Rajkumar Kore et al., "Synthesis of Dicationic Ionic Liquids and their Application in the Preparation of Hierarchical Zeolite Beta," *Chemistry A European Journal* 2011, 17, 14360-14365. DOI: 10.1002/chem.201102946.

Rajkumar Kore et al., "Replacing HF or ATC13 in the Acylation of Isobutylbenzene with Chloroaluminate Ionic Liquids," *ACS Sustainable Chem. Eng.* 2020, 8, 10330-10334.

The International Search Report and Written Opinion issued on Feb. 1, 2022 for international patent application No. PCT/US21/46882; pp. 1-11.

Zetryana Puteri Tachrim et al., "Trifluoromethanesulfonic Acid as Acylation Catalyst: Special Feature for C- and/or O-Acylation Reactions," *Catalysts* 2017, 7, 40; pp. 1-28. DOI: 10.3390/catal7020040.

The Science Snail. "Synthesis of ibuprofen from benzene," Oct. 11, 2018. https://www.sciencesnail.com/science/synthesis-of-ibuprofen-from-benzene; pp. 1-12.

* cited by examiner

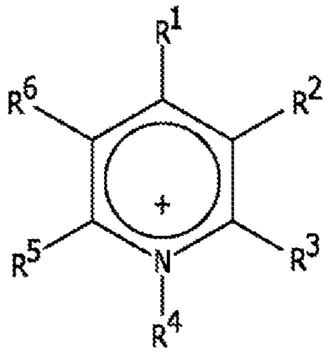
PYRIDINIUM
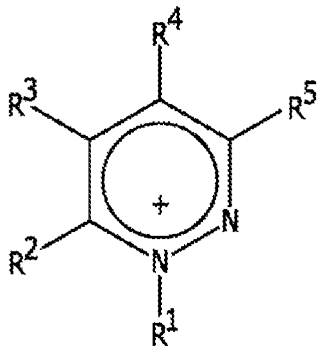
PYRIDAZINIUM
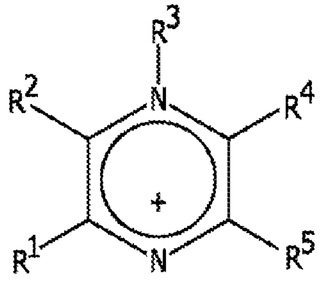
PYRIMIDINIUM
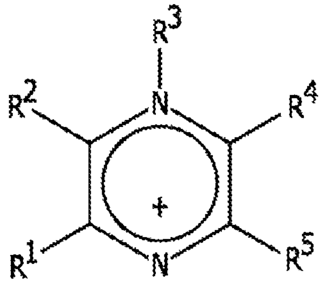
PYRAZINIUM
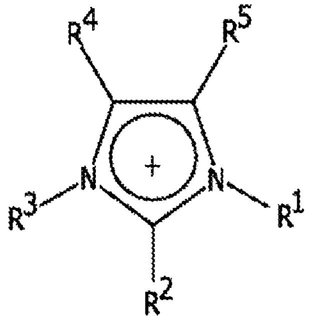
IMIDAZOLIUM
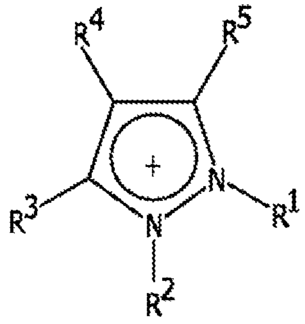
PYRAZOLIUM
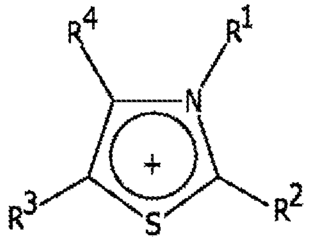
THIAZOLIUM
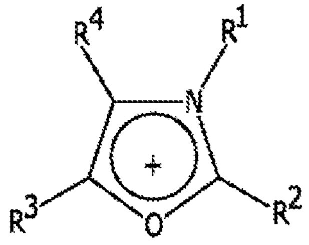
OXAZOLIUM
FIG. 1A

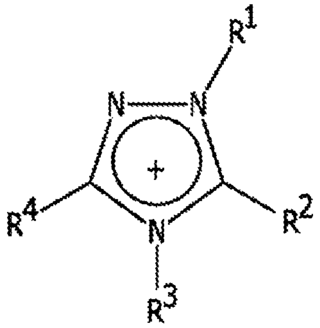
TRIAZOLIUM
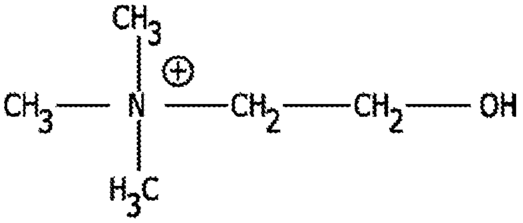
CHOLINE
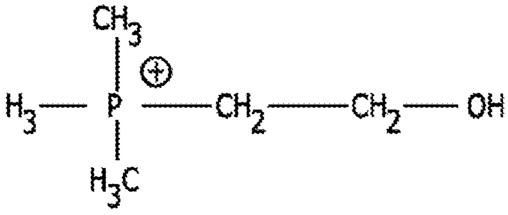
PHOSPHONIUM CHOLINE
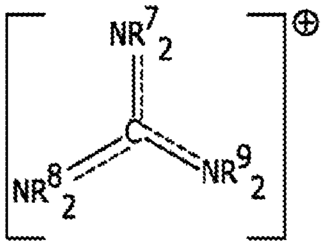
GUANIDINIUM
FIG. 1B
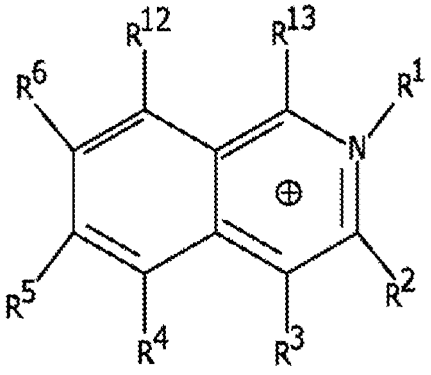
ISOQUINOLINIUM
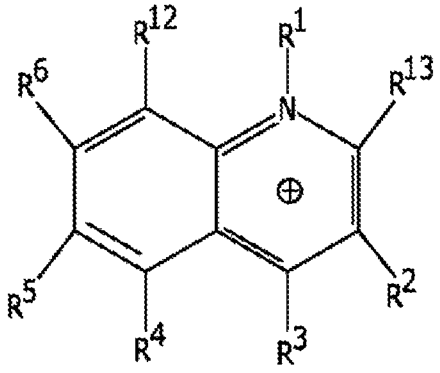
QUINOLINIUM
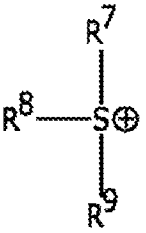
SULFONIUM
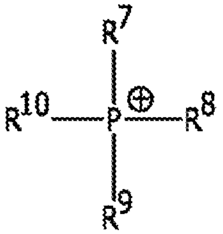
PHOSPHONIUM
AND
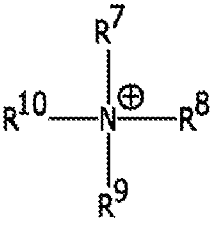
AMMONIUM
FIG. 1C CATIONS:
FORMULA A
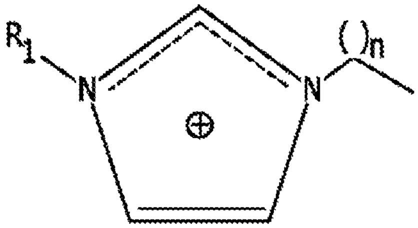
$[C_{R1}C_nim]^+$
(n=0-18; R1=H OR ALKYL GROUP)
FORMULA B
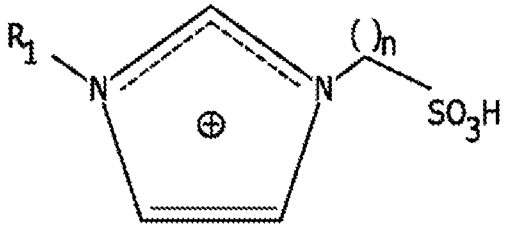
$[C_{R1}Im-C_n-SO_3H]^+$
(n=0,3,4,5; R1=H OR ALKYL GROUP )
FORMULA C
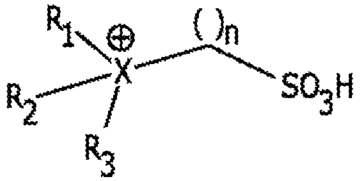
$[X_{R1R2R3}-C_n-SO_3H]^+$
(n=0,3,4,5; X=N,P,S; $R_1/R_2/R_3$=H, ALKYL GROUP)
FORMULA D
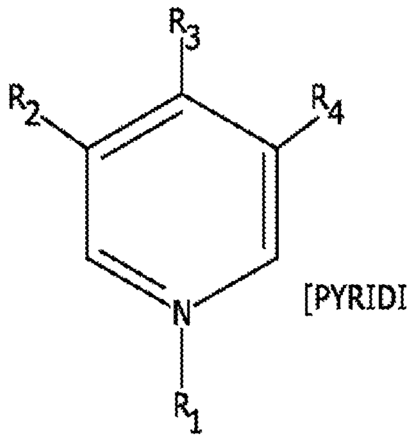
$[PYRIDINIUM]^+$
$R_2/R_3/R_4$=H, ALKYL GROUP
$R_1$=H, ALKYL GROUP, $C_n-SO_3H$(n=0,3,4,5)
FORMULA E
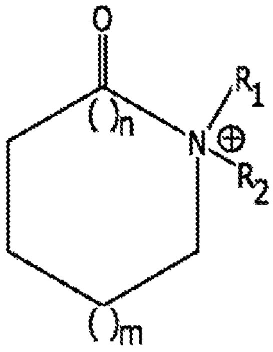
(n=0,1; m=0,1,2)
$R_1/R_2/$=H, ALKYL GROUP ,$C_n-SO_3H$(n=0,3,4,5)
FIG. 1D BASES:
FORMULA F
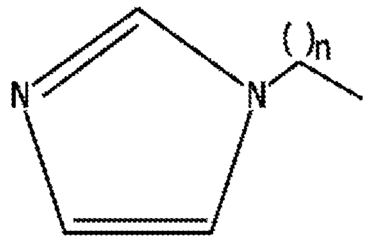
n=0 TO 18
FORMULA G
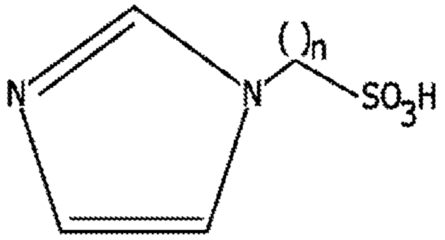
n=0,3,4,5
FORMULA H
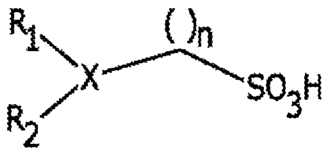
n=0,3,4,5; X=N,P,S;
$R_1/R_2$=H, ALKYL GROUP
FORMULA I
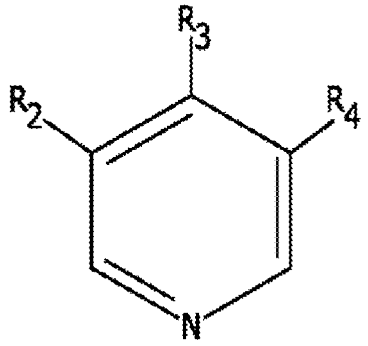
$R_2/R_3/R_4$=H, ALKYL GROUP
FORMULA J
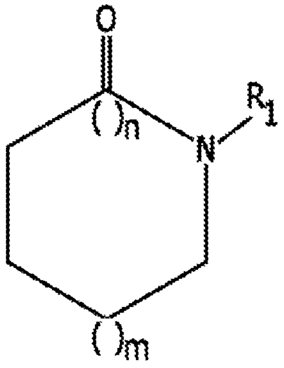
n=0,1; m=0,1,2
$R_1$=H, ALKYL GROUP,
$C_n$-$SO_3H$(n=0,3,4,5)
FIG. 1E

ANIONS:

$HSO_4^{-}$ $CH_3SO_3^{-}$ $CF_3SO_3^{-}$ $HCF_2(CF_2)_nSO_3^{-}$ $\overset{-}{N}\text{-}(SO_2CF_3)_2$ 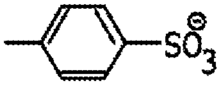

$R\text{-}SO_3^{-}$ $CF_3CO_2^{-}$ $\overset{-}{N}\text{-}(CN)_2$ $BF_4^{-}$ $PF_6^{-}$ [HALIDE]$^{-}$

FIG. 2

ACIDS:

| | | | |
|---|---|---|---|
| $H_2SO_4$<br>SULFURIC ACID | $CH_3SO_3H$<br>METHANESULFONIC ACID | $CF_3SO_3H$<br>TRIFLIC ACID (TFMSA) | $HCF_2CF_2SO_3H$<br>TETRAFLUOROETHANESULFONIC ACID(TFESA) |
| $CH_3C_6H_4SO_3H$<br>TOLUENESULFONIC ACID | $CF_3CO_2H$<br>TRIFLUOROACETIC ACID | $H_3PO_4$<br>PHOSPHORIC ACID | |

FIG. 3

BASE/AROMATICS:

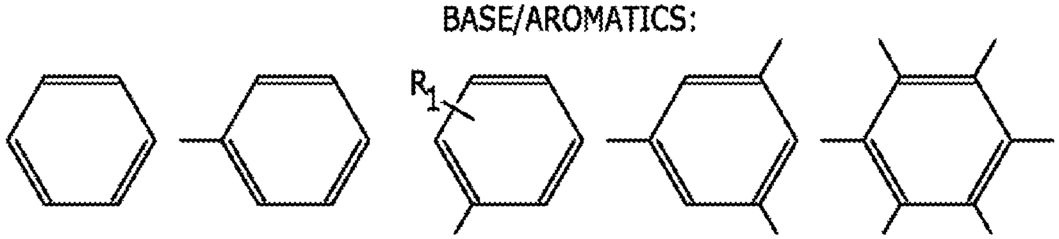

BENZENE TOLUENE o/m/p-XYLENES MESITYLENE HEXAMETHYLBENZENE

FIG. 4

Isobutylbenzene
4-Isobutylacetophenone
(Ibuprofen Intermediate)
Ibuprofen

PROCESSES FOR THE ACYLATION OF AN AROMATIC COMPOUND

CROSS-REFERENCE TO RELATED APPLICATIONS

The present application is a National Stage of International Application No. PCT/US21/46882, filed Aug. 20, 2021, which claims priority to U.S. provisional patent application 63/069,332 that was filed Aug. 24, 2020, the entire contents of both of which are incorporated herein by reference.

BACKGROUND

Friedel-Crafts acylation of aromatic compounds is an important reaction in the production of aromatic ketones. These aromatic ketones are largely used as intermediates in the synthesis of pharmaceuticals, naproxen, dextromethorphan, ibuprofen and dyes, fragrances, and agrochemicals. The product 4-isobutylacetophenone obtained from the acylation of isobutylbenzene is largely used as an intermediate for the synthesis of ibuprofen and other pharmaceuticals. The traditional catalysts used to synthesize 4-isobutylacetophenone from acylation of isobutylbenzene are $AlCl_3$, HF, and zeolites. Due to its low activity, $AlCl_3$ is used in higher than stoichiometric amounts, results in a larger amount of waste, and is non-regenerable after the reaction. HF is an extremely toxic, volatile, and corrosive chemical, and is also typically used in a higher than stoichiometric amount relative to isobutylbenzene. A solid acid catalyst such as an acidic zeolite was investigated in the reaction but the yield obtained was very low (<6%). Recently, a chloroaluminate ionic liquid (IL)-based catalyst was also investigated in the reaction but these are moisture sensitive materials and difficult to handle.

SUMMARY

The present disclosure provides processes for the acylation of aromatic compounds, including isobutylbenzene.

Processes for acylating an aromatic compound are provided. In embodiments, such a process comprises combining an aromatic compound, an acylating agent, and a catalyst composition under conditions to induce acylation of the aromatic compound with the acylating agent, the catalyst composition comprising components selected from the group consisting of a sulfonic acid of formula R—$SO_3$H, wherein R is a linear alkyl group substituted with one or more halogen atoms; an ionic liquid and an acid; an acid and a base capable of forming an ionic liquid with the acid; an ionic liquid, an acid, and an aromatic; and an acid, a base capable of forming an ionic liquid with the acid, and an aromatic. The ionic liquid does not comprise a metal halide and the catalyst composition is free of a metal halide and the aromatic, if present in the catalyst composition, is not the aromatic compound being acylated.

In other embodiments, such a process comprises combining an aromatic compound, an acylating agent, and a catalyst composition under conditions to induce acylation of the aromatic compound with the acylating agent, the catalyst composition comprising a sulfonic acid of formula R—$SO_3$H, wherein R is a linear alkyl group substituted with one or more halogen atoms, wherein the catalyst composition is free of a metal halide and wherein a mole ratio of the catalyst composition to the acylating agent is no more than 0.5:1.

Other principal features and advantages of the disclosure will become apparent to those skilled in the art upon review of the following drawings, the detailed description, and the appended claims.

BRIEF DESCRIPTION OF THE DRAWINGS

Illustrative embodiments of the disclosure will hereafter be described with reference to the accompanying drawings.

FIGS. 1A-1C show illustrative cations which may be used to form an ionic liquid for use in the present catalyst compositions.

FIG. 1D shows illustrative cations which may be used to form an ionic liquid for use in the present catalyst compositions.

FIG. 1E shows illustrative bases for use in the present catalyst compositions.

FIG. 2 shows illustrative anions which may be used to form an ionic liquid for use in the present catalyst compositions.

FIG. 3 shows illustrative acids for use in the present catalyst compositions.

FIG. 4 shows illustrative aromatics for use in the present catalyst compositions.

DETAILED DESCRIPTION

Figure 5:
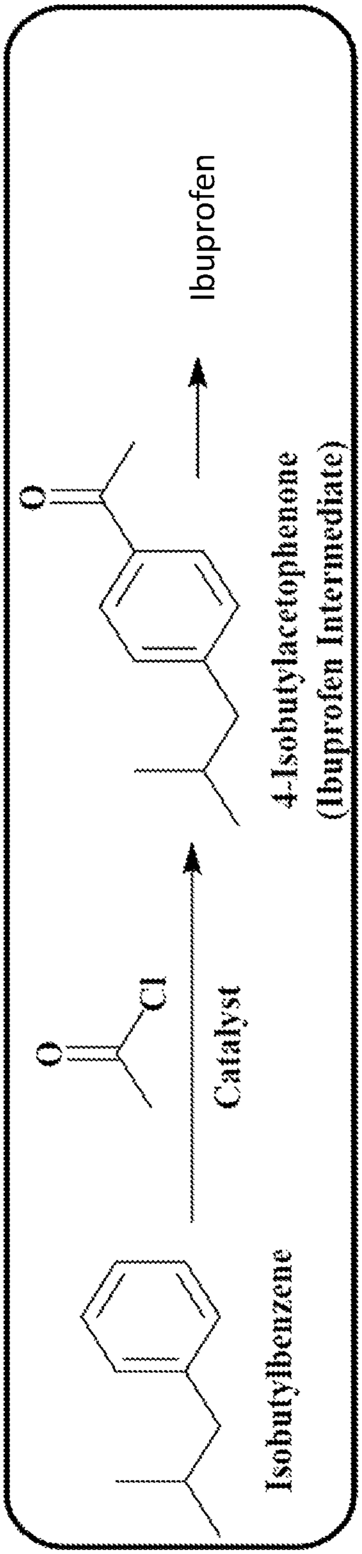
FIG. 5 shows the reaction scheme for the acylation of isobutylbenzene with acetyl chloride, which may be carried out using the present catalyst compositions.

The present disclosure provides a process for the acylation of aromatic compounds using certain catalyst compositions. At least some embodiments of the process achieve high conversion values (e.g., >99.9%), high selectivities (e.g., 95%), or both. The present processes are more environmentally friendly as compared to existing processes, e.g., those based on HF. Additional advantages include, but are not limited to, non-toxic and moisture stable catalyst composition, much less catalyst composition required, easy recovery of the catalyst composition, and tunable product selectivity via acidity of the catalyst composition.

The present catalyst compositions are multicomponent ionic systems which are typically liquids near room temperature (e.g., 20 to 25° C.). Components which may be used to form the catalyst compositions include certain ionic liquids; acids; bases; and aromatics. Each of these components are described below, followed by a description of various catalyst compositions formed therefrom.

Ionic Liquids

Various ionic liquids may be used to form the present catalyst compositions. As used in the present disclosure, "ionic liquid" refers to salts composed of at least one cation and at least one anion and are being used in their fluid state. They are generally in their fluid state at or below a temperature of about 100° C.

Representative examples of ionic liquids suitable for use herein are included among those that are described in sources such as *J. Chem. Tech. Biotechnol.,* 68:351-356 (1997); *Chem. Ind.,* 68:249-263 (1996); *J. Phys. Condensed Matter,* 5: (supp 34B):899-8106 (1993); *Chemical and Engineering News*, Mar. 30, 1998, 32-37; *J. Mater. Chem.,* 8:2627-2636 (1998); *Chem. Rev.,* 99:2071-2084 (1999); and WO 05/113,702 (and references cited therein), each of which is by this reference incorporated herein for the purpose of the ionic liquids disclosed therein.

Many ionic liquids are formed by reacting a nitrogen-containing heterocyclic ring, preferably a heteroaromatic ring, with an alkylating agent (e.g., an alkyl halide) to form a quaternary salt, and performing ion exchange or other suitable reactions with various Lewis acids or their conjugate bases to form the ionic liquid. Some ionic liquids are formed by reacting N—, P—, and S— compounds with a Bronsted acid to quaternize the heteroatom. Examples of suitable heteroaromatic rings include substituted pyridines, imidazole, substituted imidazole, pyrrole and substituted pyrroles. These rings can be alkylated with virtually any straight, branched or cyclic $C_{1-20}$ alkyl group, but the alkyl groups are preferably $C_{1-16}$ groups. Various trialkylphosphines, thioethers and cyclic and non-cyclic quaternary ammonium salts may also be used for this purpose. Ionic liquids suitable for use herein may also be synthesized by salt metathesis, by an acid-base neutralization reaction, or by quaternizing a selected nitrogen-containing compound. The synthesis of other ionic liquids suitable for use herein is described in U.S. Pat. No. 8,715,521, which is by this reference incorporated in its entirety as a part hereof for all purposes. Ionic liquids may also be obtained commercially from several companies such as Merck (Darmstadt, Germany), BASF (Mount Olive N.J.), Fluka Chemical Corp. (Milwaukee Wis.), and Sigma-Aldrich (St. Louis Mo.), Iolitec-Ionic Liquids Technologies, GmbH (Heilbronn, Germany) and Proionic (Graz, Austria).

Ionic liquids suitable for use herein comprise a cation and an anion. A variety of cations and anions may be used. Either or both of the ions may be fluorinated. However, in embodiments, neither of the ions are fluorinated. The ionic liquid may include more than one type of cation, more than one type of anion, or both. However, the ionic liquid may include a single type of cation and a single type of anion. When the ionic liquid includes a single type of cation and a single type of anion, however, this does not preclude some amount of ion exchange with other ions in the catalyst composition (derived from other components of the catalyst composition).

In embodiments, the cation is selected from the group consisting of cations represented by the structures of the formulae shown in FIGS. 1A-1C. In these formulae, the following provisos apply:

(a) $R^1$, $R^2$, $R^3$, $R^4$, $R^5$, $R^6$, $R^{12}$ and $R^{13}$ are independently selected from the group consisting of:

(i) H;

(ii) halogen such as F;

(iii) —$CH_3$, —$C_2H_5$, or $C_3$ to $C_{25}$ straight-chain, branched or cyclic alkane or alkene groups, optionally substituted with at least one member selected from the group consisting of Cl, Br, F, I, OH, $NH_2$ SH, and $SO_3H$;

(iv) —$CH_3$, —$C_2H_5$, or $C_3$ to $C_{25}$ straight-chain, branched or cyclic alkane or alkene groups comprising one to three heteroatoms selected from the group consisting of O, N, Si and S, and optionally substituted with at least one member selected from the group consisting of Cl, Br, F, I, OH, $NH_2$ and SH;

(v) $C_6$ to $C_{25}$ unsubstituted aryl, or $C_6$ to $C_{25}$ unsubstituted heteroaryl, groups having one to three heteroatoms independently selected from the group consisting of O, N, Si and S, wherein the unsubstituted aryl or unsubstituted heteroaryl may be bonded to the structure via an alkyl (e.g., —$CH_2$—) spacer group;

(vi) $C_6$ to $C_{25}$ substituted aryl, or $C_6$ to $C_{25}$ substituted heteroaryl, groups having one to three heteroatoms independently selected from the group consisting of O, N, Si and S; wherein the substituted aryl or substituted heteroaryl may be bonded to the structure via an alkyl (e.g., —$CH_2$—) spacer group; and wherein said substituted aryl or substituted heteroaryl has one to three substituents independently selected from the group consisting of:

(A) —$CH_3$, —$C_2H_5$, or $C_3$ to $C_{25}$ straight-chain, branched or cyclic alkane or alkene groups, optionally substituted with at least one member selected from the group consisting of Cl, Br, F, I, OH, $NH_2$ and SH, (B) OH, (C) $NH_2$, and (D) SH; and (vii) —$(CH_2)_nSi(CH_2)_mCH_3$, —$(CH_2)_nSi(CH_3)_3$, —$(CH_2)_nOSi(CH_3)_m$, where n is independently 1-4 and m is independently 0-4;

(b) $R^7$, $R^8$, $R^9$, and $R^{10}$ are independently selected from the group consisting of:

(i) —$CH_3$, —$C_2H_5$, or $C_3$ to $C_{25}$ straight-chain, branched or cyclic alkane or alkene groups, optionally substituted with at least one member selected from the group consisting of Cl, Br, F, I, OH, $NH_2$, SH and $SO_3H$;

(ii) —$CH_3$, —$C_2H_5$, or $C_3$ to $C_{25}$ straight-chain, branched or cyclic alkane or alkene groups comprising one to three heteroatoms selected from the group consisting of O, N, Si and S, and optionally substituted with at least one member selected from the group consisting of Cl, Br, F, I, OH, $NH_2$ and SH;

(iii) $C_6$ to $C_{25}$ unsubstituted aryl, or $C_6$ to $C_{25}$ unsubstituted heteroaryl, groups having one to three heteroatoms independently selected from the group consisting of O, N, Si and S; and (iv) $C_6$ to $C_{25}$ substituted aryl, or $C_6$ to $C_{25}$ substituted heteroaryl, groups having one to three heteroatoms independently selected from the group consisting of O, N, Si and S, and wherein the substituted aryl or substituted heteroaryl group has one to three substituents independently selected from the group consisting of:

(A) —$CH_3$, —$C_2H_5$, or $C_3$ to $C_{25}$ straight-chain, branched or cyclic alkane or alkene groups, optionally substituted with at least one member selected from the group consisting of Cl, Br, F, I, OH, $NH_2$ and SH, (B) OH, (C) $NH_2$, and (D) SH; and (v) —$(CH_2)_nSi(CH_2)_mCH_3$, —$(CH_2)_nSi(CH_3)_3$, —$(CH_2)_nOSi(CH_3)_m$, where n is independently 1-4 and m is independently 0-4; and (c) optionally, at least two of $R^1$, $R^2$, $R^3$, $R^4$, $R^5$, $R^6$, $R^7$, $R^8$, $R^9$, and $R^{10}$ can together form a cyclic or bicyclic alkyl or alkenyl group.

In embodiments, the ionic liquid comprises a cation selected from one or more members of the group consisting of pyridinium, pyridazinium, pyrimidinium, pyrazinium, imidazolium, pyrazolium, thiazolium, oxazolium, triazolium, phosphonium, ammonium, benzyltrimethylammonium, choline, cholinium, dimethylimidazolium, guanidinium, phosphonium choline, lactam, sulfonium, tetramethylammonium, and tetramethylphosphonium.

In embodiments, the ionic liquid comprises an anion selected from one or more members of the group consisting of: $[CH_3CO_2]^-$, $[HSO_4]^-$, $[CH_3OSO_3]^-$, $[C_2H_5OSO_3]^-$, $[CH_3C_6H_4SO_3]^-$ ($[TSO]^-$), $[CO_3]^{2-}$, $[HCO_3]^-$, $[NO_2]^-$, $[NO_3]^-$, $[SO_4]^{2-}$, $[PO_3]^{3-}$, $[HPO_3]^{2-}$, $[H_2PO_3]^{1-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$, carborates optionally substituted with alkyl or substituted alkyl; carboranes optionally substituted with alkylamine, substituted alkylamine, alkyl or substituted alkyl; and a fluorinated anion.

In embodiments, the ionic liquid comprises an anion selected from one or more members of the group consisting of aminoacetate, ascorbate, benzoate, catecholate, citrate, dimethylphosphate, formate, fumarate, glycolate, glyoxylate, iminodiacetate, isobutyrate, kojate, lactate, levulinate, oxalate, pivalate, propionate, pyruvate, salicylate, succinamate, succinate, tiglate, tetrafluoroborate, tetrafluoroethanesulfonate, tropolonate, $[CH_3CO_2]^-$, $[HSO_4]^-$, $[CH_3SO_3]^-$, $[CH_3OSO_3]^-$, $[C_2H_5OSO_3]^-$, $[CH_3C_6H_4SO_3]^-$, $[CO_3]^{2-}$, $[HCO_3]^-$, $[NO_2]^-$, $[NO_3]^-$, $[SO_4]^{2-}$, $[PO_3]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$, $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[CHF_2CF_2CF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]$, $[CF_3CF_2OCF_2CF_2SO_3]^-$, $[(CF_2HCF_2SO_2)_2N]$—, $[(CF_3CFHCF_2SO_2)_2N]^-$, $[N(CN)_2]^-$, $F^-$, and anions represented by the structure of the following formula, $[R_{11}COO]^-$, wherein $R^{11}$ is selected from the group consisting of:

(i) —$CH_3$, —$C_2H_5$, or $C_3$ to $C_{10}$ straight-chain, branched or cyclic alkane or alkene groups, optionally substituted with at least one member selected from the group consisting of Cl, Br, F, I, OH, $NH_2$ and SH;

(ii) —$CH_3$, —$C_2H_5$, or $C_3$ to $C_{10}$ straight-chain, branched or cyclic alkane or alkene groups that contain one to three heteroatoms selected from the group consisting of O, N, Si and S, and are optionally substituted with at least one member selected from the group consisting of Cl, Br, F, I, OH, $NH_2$ and SH;

(iii) $C_6$ to $C_{10}$ unsubstituted aryl, or $C_6$ to $C_{10}$ unsubstituted heteroaryl, groups having one to three heteroatoms independently selected from the group consisting of O, N, Si and S; and (iv) $C_6$ to $C_{10}$ substituted aryl, or $C_6$ to $C_{10}$ substituted heteroaryl, groups having one to three heteroatoms independently selected from the group consisting of O, N, Si and S; and wherein the substituted aryl or substituted heteroaryl group has one to three substituents independently selected from the group consisting of:

(A) —$CH_3$, —$C_2H_5$, or $C_3$ to $C_{10}$ straight-chain, branched or cyclic alkane or alkene groups, optionally substituted with at least one member selected from the group consisting of Cl, Br, F, I, OH, $NH_2$ and SH, (B) OH, (C) $NH_2$, and (D) SH.

In embodiments, the cation of the ionic liquid is selected from an imidazolium, an ammonium, a phosphonium, a sulfonium, a pyridinium, and a lactam. The cation may be protic or aprotic. The proton in the protic cation may be from a —$SO_3H$ group. Illustrative imidazolium, ammonium, phosphonium, sulfonium, pyridinium, and lactam cations are shown in FIG. 1D. In embodiments, the cation of the ionic liquid is selected from the group consisting of cations represented by the structures of the formulae shown in FIG. 1D, i.e., Formulae A-E. In these formulae, the provisos noted in FIG. 1D apply.

In embodiments, the cation of the ionic liquid is an imidazolium having Formula A or B shown in FIG. 1D, an imidazolium having the formula shown in FIG. 1A, or an ammonium having the formula shown in FIG. 1C. In these formulae, the provisos noted in FIG. 1D and FIGS. 1A, 1C apply, respectively.

The anion of the ionic liquid may be a sulfonate. The sulfonate may have the formula $[R—SO_3]^-$, wherein R is an alkyl group or an aryl group. The alkyl group may be a linear alkyl group in which the number of carbons may range from, e.g., 1 to 12. The alkyl group may be unsubstituted, by which it is meant the alkyl group contains only carbon and hydrogen and no heteroatoms. The alkyl group may be substituted, by which it is meant an unsubstituted alkyl group in which one or more bonds to a carbon(s) or hydrogen(s) are replaced by a bond to non-hydrogen and non-carbon atoms. Non-hydrogen and non-carbon atoms include, e.g., a halogen atom such as F. Aryl groups may be unsubstituted or substituted as described above with respect to alkyl groups. However, substituted aryl groups also refer to an unsubstituted monocyclic aryl group in which one or more carbon atoms are bonded to an alkane. The alkane may be linear, have various numbers of carbon, and may be unsubstituted or substituted as described above with respect to alkyl groups.

The anion may be a carboxylate. The carboxylate may have the formula $[R—CO_2]^-$, wherein R is an alkyl group as described above with respect to sulfonate. This means that fluoroalkane carboxylates are encompassed, e.g., R may be $CF_3$, $HCF_2CF_2$, $CF_3HFCCF_2$, etc. The carboxylate (or fluoroalkane carboxylate) may be a dicarboxylate, a tricarboxylate, a tetracarboxylate, etc. Other anions which may be used include $[HSO_4]^-$, dicyanamide; and inorganic anions such as $[BF_4]^-$, $[PF_6]^-$, and a halide. Illustrative anions are shown in FIG. 2. In $[HCF_2(CF_2)_nSO_3]^-$, n may be 0, 1, 2, or 3.

In embodiments, the anion of the ionic liquid is $[HSO_4]^-$ or $[HCF_2CF_2SO_3]^-$.

Ionic liquids disclosed in the following references may also be used: U.S. Pat. Nos. 8,771,626; 8,779,220; 8,808,659; U.S. Pat. Pub. No. 20100331599; U.S. Pat. Nos. 7,432,408; 9,914,674; U.S. Pat. Pub. No. 20160289138; U.S. Pat. Pub. No. 20140113804; U.S. Pat. Pub. No. 20160167034; U.S. Pat. Pub. No. 20150315095; and U.S. Pat. Nos. 9,567,273; 9,346,042; 9,260,668; 9,096,487; 8,692,048; 8,653,318; 8,633,346; 8,569,561; 8,552,243; and 7,285,698. Each of these is by this reference incorporated herein for the purpose of the ionic liquids disclosed therein.

In the ionic liquids, various relative amounts of the cation(s) and anion(s) may be used. In embodiments, the molar ratio of the cation:anion is in the range of from 1:1 to 4:1.

Illustrative specific ionic liquids are also provided in the Examples, below.

In embodiments, the following provisos apply: the ionic liquid is not a haloaluminate (e.g., chloroaluminate), a halozincate, a haloferrate, a halogallate, a halostannate, a haloindate, a halochromate, a halocuprate, a halotitannate, a halozirconate, or a halopalladate and the ionic liquid is not formed from a metal halide (thus, neither the cation(s) nor the anion(s) of the ionic liquid are derived from such a metal halide). In such embodiments, the catalyst composition is free of such ionic liquids and free of a metal halide. In embodiments, the ionic liquid is not formed from a non-metal halide (thus, neither the cation(s) nor the anion(s) of the ionic liquid are derived from such a non-metal halide). In such embodiments, the catalyst composition is free of such ionic liquids and free of a non-metal halide. The term "halide" may be used to refer to both metal and non-metal halides. The embodiments in this paragraph do not preclude the use of certain halogenated cation(s), anion(s) (e.g., $HCF_2CF_2SO_3^-$), halogenated acids (e.g., haloalkane sulfonic acids), halogenated bases, and halogenated aromatic compounds (e.g., halogenated benzene). Throughout the present disclosure, the term "free" means that the amount of the relevant component is zero or sufficiently close to zero to have no material effect on the properties of the catalyst composition.

Known methods may be used to prepare ionic liquids. Other ionic liquids may be commercially available. Illustrative methods for synthesizing ionic liquids are described in the Examples, below.

Acids

Various acids may be used to form the present catalyst compositions, including combinations of different types of acids. However, a single type of acid may also be used. Mineral acids may be used, e.g., sulfuric acid, phosphoric acid, hydrofluoric acid, hydrochloric acid.

Sulfonic acids may be used. The sulfonic acid may have the formula $R—SO_3H$, wherein R is an alkyl group or an aryl group. The alkyl group may be linear, branched, or cyclic and may have a number of carbons in a range from, e.g., 1 to 12. The alkyl group may be unsubstituted, by which it is meant the alkyl group contains only carbon and hydrogen and no heteroatoms. The alkyl group may be substituted, by which it is meant an unsubstituted alkyl group in which one or more bonds to a carbon(s) or hydrogen(s) are replaced by a bond to non-hydrogen and non-carbon atoms. Non-hydrogen and non-carbon atoms include, e.g., a halogen atom such as F, Cl, Br, and I. Aryl groups may be unsubstituted or substituted as described above with respect to alkyl groups. However, substituted aryl groups also refer to an unsubstituted monocyclic aryl group in which one or more carbon atoms are bonded to an alkane. The alkane may be linear, branched, or cyclic, have various numbers of carbon atoms, and may be unsubstituted or substituted as described above with respect to alkyl groups.

Carboxylic acids may be used. The carboxylic acid may have the formula $R—CO_2H$, wherein R is an alkyl or an aryl group as described above with respect to sulfonic acid.

Illustrative specific acids are shown in FIG. 3. In embodiments, the acid is triflic acid. In embodiments, the acid is tetrafluoroethanesulfonic acid.

In embodiments, the acid is not hydrofluoric acid and the catalyst composition is free of hydrofluoric acid.

Bases

In embodiments, a base is used which forms, in situ, an ionic liquid when combined with any of the disclosed acids in forming the catalyst composition. Thus, any base which generates any of the cations described in "Ionic Liquids," above, upon combination with any of the disclosed acids may be used. By way of illustration, the base may be an imidazole, an ammonia, a phosphine, a sulfide, a pyridine, or a lactam. The base be selected from the group of compounds having any of the formulae shown in FIG. 1E, i.e., Formulae F-J. In these formulae, the alkyl group may be a linear alkyl group in which the number of carbons may range from, e.g., 1 to 12. The alkyl group may be unsubstituted, by which it is meant the alkyl group contains only carbon and hydrogen and no heteroatoms. The alkyl group may be substituted, by which it is meant an unsubstituted alkyl group in which one or more bonds to a carbon(s) or hydrogen(s) are replaced by a bond to non-hydrogen and non-carbon atoms. Non-hydrogen and non-carbon atoms include, e.g., a halogen atom such as F.

In embodiments, the base is an imidazole, e.g., having Formula F or Formula G in FIG. 1E In embodiments, the base is an ammonia.

The catalyst composition may be formed from different types of bases. However, a single type of base may also be used.

Aromatics

Various aromatics may be used to form the present catalyst compositions, including combinations of different types of aromatics. However, a single type of aromatic may also be used.

The aromatic may be monocyclic having one or more unfused aromatic rings. Each aromatic ring may have various members, e.g., a 5-membered ring, a six-membered ring, etc. Monocyclic aromatics may be unsubstituted, by which it is meant the aromatic contains only carbon and hydrogen and no heteroatoms. Unsubstituted monocyclic aromatics have a single aromatic ring. Monocyclic aromatics may be substituted, by which it is meant an unsubstituted aromatic in which one or more bonds to a carbon(s) or hydrogen(s) are replaced by a bond to non-hydrogen and non-carbon atoms. Non-hydrogen and non-carbon atoms include, e.g., a halogen atom such as F, Cl, Br; O; N; etc. However, substituted monocyclic aromatics also refer to an unsubstituted monocyclic aromatic in which one or more carbon atoms are bonded to an unsubstituted or substituted alkane or another unsubstituted or substituted monocyclic aromatic. The alkane may be linear or branched, have various numbers of carbon atoms, and may be unsubstituted or substituted as described above with respect to the definition of alkyl groups in "Acids." Thus, monocyclic aromatics include benzene, biphenyl, triphenyl, furan, pyridine, pyrrole, etc. (each which may be unsubstituted or substituted).

The monocyclic aromatic may have the formula $C_6R_6$, wherein each R is independently selected from hydrogen, a halogen, and an alkyl group. The alkyl group may be linear or branched have various numbers of carbon atoms and may be unsubstituted or substituted as described above with respect to the definition of alkyl groups in "Acids." Illustrative such monocyclic aromatics are shown in FIG. 4.

Polycyclic aromatics may be used. Polycyclic aromatics have fused aromatic rings (e.g., two, three, etc. rings). Each ring may have various members and may be unsubstituted or substituted as described for monocyclic aromatics. Naphthalene, anthracene, phenanthrene, benzofuran are illustrative polycyclic aromatics.

In embodiments, the aromatic is hexamethylbenzene.

Similar to the bases described above, it is noted that the aromatic used in the catalyst composition may be one which forms, in situ, an ionic liquid when combined with the acid to form the catalyst composition.

Catalyst Compositions

One or more of any of the disclosed ionic liquids, acids, bases, and aromatics may be used to form the present catalyst compositions. As noted above, ion exchange generally occurs between the various components of the catalyst compositions, once formed. In addition, there may be some overlap between compounds suitable for the various components, e.g., some compounds may be suitable as a base and an aromatic. However, catalyst compositions described as comprising, e.g., an "ionic liquid," an "acid", and an "aromatic" refer to catalyst compositions in which separate and distinct chemicals have been combined to form the catalyst composition regardless of how the various ions may subsequently rearrange/associate therein. For example, a catalyst composition described as comprising an "ionic liquid," an "acid", and an "aromatic" means that a chemically distinct ionic liquid, a chemically distinct acid, and a chemically distinct aromatic were combined to form the catalyst composition. As another example, a catalyst composition described as comprising an ionic liquid and an acid refers to compositions in which a chemically distinct ionic liquid and a chemically distinct acid were combined to form the catalyst composition.

The particular component or combination of components may be selected to achieve certain behavior, e.g., desired conversion or desired product selectivity. Specific combinations are illustrated in the Examples below, but these are not intended to be limiting. Similarly, for catalyst compositions comprising more than one component, the components may be present at various amounts selected to achieve certain behavior. By way of illustration, as shown in the Examples, below, it has been found that both conversion and product selectivity are particularly sensitive to the type and amount of the acid component used. (See Table 2.)

Table 1, below, lists catalyst compositions which may be used. The various components may be selected from those described above. More than one type of each component may be used, i.e., more than one type of ionic liquid/base, more than one type of acid, and/or more than one type of aromatic. In other such embodiments, a single type of each component may be used. The provisos described above may apply, e.g., no metal halides; no hydrofluoric acid. The parameters x and y refer to weight percents, as further described below.

TABLE 1

| Catalyst Compositions. |
|---|
| $[IL]_x$-$[Acid]_{(100-x)}$ |
| $[IL]_x$-$[Acid]_{(100-x)}$-$[Aromatic]_y$ |
| $[Base]_x$-$[Acid]_{(100-x)}$ |
| $[Base]_x$-$[Acid]_{(100-x)}$-$[Aromatic]_y$ |

In the catalyst compositions $[IL]_x$-$[Acid]_{100-x}$ and $[Base]_x$-$[Acid]_{(100-x)}$, the parameter x refers to a weight (wt) %, i.e., ((weight of the ionic liquid/base)/(combined weight of the ionic liquid/base and the acid))*100. In embodiments, x is in a range of from 0.5 wt % to 90 wt % and the acid is present at an amount in a range of from 99.5 wt % to 10 wt %. In embodiments, x is 0 and only the acid is present. This includes embodiments in which the ionic liquid/base is present at an amount in a range of from 2 wt % to 80 wt %, from 5 wt % to 60 wt %, from 5 wt % to 30 wt % or from 5 wt % to 20 wt % and the acid is present at an amount in a range of from 98 wt % to 20 wt %, from 95 wt % to 40 wt %, from 95 wt % to 70 wt % or from 95 wt % to 80 wt %, respectively.

In the catalyst compositions $[IL]_x$-$[Acid]_{(100-x)}$-$[Aromatic]_y$ and $[Base]_x$-$[Acid]_{(100-x)}$-[Aromatic]y, x is as defined above and y refers to ((weight of the aromatic)/(combined weight of the ionic liquid/base, and acid))*100. In embodiments, the aromatic component may be present in any amount up to its saturation point in the composition. In embodiments, y is in a range of from of 0.1 wt % to 25 wt %. This includes from 1 wt % to 15 wt %, 1 wt % to 10 wt %, from 3 wt % to 9 wt %, or from 5 wt % to 8 wt %. In embodiments, y may be in a range of from 0.1 wt % to 100 wt % or from 0.1 wt % to 50 wt %.

An amount of water may be present in the catalyst composition. However, in embodiments, the catalyst composition consists or consists essentially of the components of Table 1.

Specific, illustrative catalyst compositions are provided in the Examples, below. As shown in the Examples, in embodiments, a sulfonic acid may be used as a catalyst composition. Any of the sulfonic acids described above may be used. This includes sulfonic acids having the formula R—$SO_3H$, wherein R is a linear alkyl group substituted with one or more halogen atoms. In embodiments, the halogen atom is F. The number of carbon atoms in the linear alkyl group may be from 1 to 12, 1 to 10, 1 to 8, 1 to 6 or 1 to 4.

Other components may be included in the catalyst compositions such as multi-ammonium salts/surfactants described in R. Kore, B. Satpati, R. Srivastava, *Synthesis of Dicationic Ionic Liquids and their Application in the Preparation of Hierarchical Zeolite Beta, Chemistry—A European Journal,* 17 (2011) 14360-14365 and R. Kore, R. Srivastava, B. Satpati, *ZSM-5 zeolite nanosheets with remarkably improved catalytic activity synthesized using a new class of structure directing agents, Chemistry—A European Journal,* 20 (2014) 11511-11521, both of which are hereby incorporated by reference in their entirety.

The present catalyst compositions may be made by combining the desired components (together or sequentially) at the desired relative amounts. The synthesis may be carried out while stirring and under room temperature. Other details are provided in the Examples, below.

With regards to the present catalyst compositions comprising three components, an acid, an aromatic, and either an ionic liquid or a base which forms, in situ, an ionic liquid with the acid, the following is noted. Without wishing to be bound to any particular theory, it is believed that the three components (or ions generated from the three components) may associate to form a molecular complex having unique, synergistic properties, as distinguished from a simple mixture of the individual components. In the present disclosure, terms such as "ternary complex," "clathrate," and the like may be used to describe this molecular complex. However, such terms are not intended to limit the scope of structural form of the molecular complex or catalyst composition. The term "ternary mixture" may also be used in reference to the catalyst composition. Catalyst compositions comprising two components, e.g., an acid and an ionic liquid may be referred to as "binary mixtures."

Acylation Process

The present catalyst compositions may be used in a process to acylate an aromatic compound. The phrase "aromatic compound" is used to distinguish an aromatic that may be present in the catalyst compositions. It is noted that the aromatic compound to be acylated may itself form a ternary complex with an acid and an ionic liquid/base in a catalyst composition used for the acylation. In embodiments, a catalyst composition is used for the alkylation which comprises any of the disclosed acids, an aromatic, and an ionic liquid or a base, the aromatic and the base, if present, are distinct chemical entities from the aromatic compound to be acylated. This means that either the aromatic/base are different chemical compounds from the aromatic compound to be acylated (i.e., are not the same chemical compound) or are the same chemical compound, but included separately at a separate amount in the catalyst composition.

In embodiments, a process to acylate an aromatic compound comprises combining an aromatic compound, an acylating agent, and any of the disclosed catalyst compositions under conditions to induce acylation of the aromatic compound. Under the appropriate conditions, the present catalyst compositions can catalyze the addition of an acyl group from the acylating agent to the aromatic compound (i.e., induce acylation). As further described below, the aromatic compound may be substituted and the acyl group may be added to the aromatic compound at its para position. The process may further comprise recovering the acylated aromatic compound from the reaction mixture.

The aromatic compound can have formula:

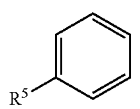

wherein $R^5$ is H, halogen, hydroxyl, substituted or unsubstituted $C_1$-$C_8$ alkyl, or substituted or unsubstituted $C_1$-$C_8$ cycloalkyl. In embodiments, $R^5$ is substituted or unsubstituted $C_1$-$C_8$ alkyl. In embodiments, $R^5$ is unsubstituted $C_1$-$C_8$ alkyl. In embodiments, $R^5$ is unsubstituted $C_4$-$C_6$ alkyl. In embodiments, $R^5$ is isobutyl. In embodiments, the aromatic compound is isobutylbenzene. Unsubstituted alkyl/cycloalkyl means the group contains only carbon and hydrogen and no heteroatoms. Substituted alkyl/cycloalkyl refers to the unsubstituted group in which one or more bonds to a carbon(s) or hydrogen(s) are replaced by a bond to non-hydrogen and non-carbon atoms. Non-hydrogen and non-carbon atoms include, e.g., a halogen atom such as F.

The acylating agent can be an acyl halide of formula:

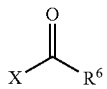

wherein X is a halogen; and $R^6$ is H, halogen, hydroxyl, substituted or unsubstituted $C_1$-$C_8$ alkyl, substituted or unsubstituted $C_1$-$C_8$ cycloalkyl, or substituted or unsubstituted aryl. Unsubstituted and substituted alkyl/cycloalkyl have been defined above with respect to the aromatic compound. Aryl groups may be monocyclic or polycyclic as described in “Aromatics” above and may be unsubstituted or substituted as described with respect to alkyl/cycloalkyl groups. However, substituted aryl groups also refer to an unsubstituted monocyclic aryl group in which one or more carbon atoms are bonded to an alkane. The alkane may be linear, have various numbers of carbon, and may be unsubstituted or substituted as described with respect to alkyl/cycloalkyl groups.

In embodiments, X is chloride. In embodiments, $R^6$ is substituted or unsubstituted $C_1$-$C_8$ alkyl. In embodiments, $R^6$ is unsubstituted $C_1$-$C_8$ alkyl. In embodiments, $R^6$ is unsubstituted $C_1$-$C_4$ alkyl. In embodiments, $R^6$ is methyl. In embodiments, the acylating agent is acetyl chloride.

The acylating agent can be an acid anhydride of formula:

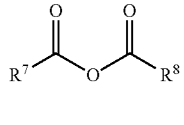

wherein $R^7$ and $R^8$ are independently H, halogen, hydroxyl, substituted or unsubstituted $C_1$-$C_8$ alkyl, substituted or unsubstituted $C_1$-$C_8$ cycloalkyl, substituted or unsubstituted aryl, or wherein, as valence permits, $R^7$ and $R^8$, together with the atoms to which they are attached, form a 4-10 membered cyclic moiety. Unsubstituted and substituted alkyl/cycloalkyl have been defined above with respect to the aromatic compound and unsubstituted and substituted aryl groups have been defined above with respect to the acyl halide.

In embodiments, $R^7$ and $R^8$ are independently H, halogen, hydroxyl, or substituted or unsubstituted $C_1$-$C_8$ alkyl. In embodiments, $R^7$ and $R^8$ are independently substituted or unsubstituted $C_1$-$C_8$ alkyl. In embodiments, $R^7$ and $R^8$ are independently unsubstituted $C_1$-$C_8$ alkyl. In embodiments, $R^7$ and $R^8$ are independently unsubstituted $C_1$-$C_4$ alkyl. In embodiments, the acylating agent is acetic anhydride.

Combinations of different types of aromatic compounds and combinations of different types of acylating agents may be used in the process.

The conditions under which acylation is induced refer to parameters such as the amount of the catalyst composition, the amount of the acylating agent; the amount of the aromatic compound; the reaction temperature; and the reaction time. These parameters may be adjusted to provide, e.g., a desired conversion and/or desired product selectivity. Illustrative values of these parameters are provided in the Examples below. Of course, the values may be scaled up as necessary for commercial processes. It is noted that due to the activity of the present catalytic compositions, generally much less of the catalytic composition is required as compared to existing processes. In embodiments, the mole ratio of the catalytic composition (total moles thereof) as compared to the acylating agent compound (total moles thereof) to be acylated is in a range of from 0.01:1 to 0.5:1. This includes from 0.01:1 to 0.2:1 and from 0.01:1 to 0.1:1. In embodiments, a mole ratio of the catalyst composition to the acylating agent is no more than 0.5:1. This includes no more than 0.2:1 and no more than 0.1:1. In other embodiments, however, a mole ratio of the catalyst composition to the acylating agent is up to 1:1 or 2:1.

A variety of reactor systems may be used to carry out the present processes, including batch, semi-continuous, continuous, and spray reactor systems. An illustrative process showing the acylation of isobutylbenzene with acetyl chloride is shown in FIG. 5.

The present catalyst compositions and acylation processes may be characterized as being capable of achieving certain properties or results, including a percent conversion and a percent selectivity (for a particular product). Known methods may be used to calculate these values. In embodiments, the conversion is at least 90%, at least 95%, at least 99% or at least 99.9%. In embodiments, the selectivity for adding an acyl group of an acylating agent to a substituted aromatic compound at its para position is at least 85%, at least 90%, at least 95%, or at least 99%. These properties may be referenced with respect to a particular set of reaction conditions, e.g., a set of reaction conditions as set forth in the Examples, below.

EXAMPLES

Example 1. Preparation of Ionic Liquids

Example 1-I: Preparation of N-methyl imidazolium hydrogen sulfate $[C_1im][HSO_4]$ IL In a 50 mL round bottom flask, equipped with a stir bar, an amount of N-methyl imidazole (4.11 g, 0.05 mol) was placed and then liquid $H_2SO_4$ acid (4.95 g, 0.05 mol) was added dropwise at 5° C. After addition, the reaction mixture was stirred at 80° C. for 4 h, giving a liquid ionic liquid $[C_1im][HSO_4]$.

Example 1-II: Preparation of N-methyl, N-sulfonic acid imidazolium tetrafluoroethane sulfonate $[C_1im\text{-}SO_3H][TFES]$ IL In a 500 mL round bottom flask, equipped with a stir bar, N-methyl imidazole (8.21 g, 0.10 mol) was reacted with chlorosulfonic acid (12.20 g, 0.104 mol) in dry dichloromethane solvent (40 mL). After addition, the reaction mixture was stirred for 12 h. The dichloromethane solvent was removed under reduced pressure, yielding a white solid. The solid was washed twice with dry diethyl ether and dried under vacuum, yielding a white solid of [$C_1$im-$SO_3$] zwitterion type of salt. For the synthesis of [$C_1$im-$SO_3$H][TFES] ionic liquid, a solid [$C_1$im-$SO_3$] zwitterionic salt (8.10 g, 0.05 mol) was placed in a 20 mL screw top borosilicate glass vial and tetrafluoroethanesulfonic acid (TFESA) (9.15 g, 0.05 mol) was added dropwise. After addition of the reactants, the reaction mixture was stirred at room temperature for 4 h, giving a brown liquid IL [$C_1$im-$SO_3$H][TFES].

Example 2. Preparation of Binary Mixtures of an Ionic Liquid and an Acid

Example 2.1-I: Preparation of ([$C_1$im-$SO_3$H][TFES])$_{10}$-(TFMSA)$_{90}$ IL In a 40 mL glass tube, equipped with a stir bar, TFMSA (0.45 g) and ionic liquid [$C_1$im-$SO_3$H][TFES] (0.05 g) was added at 10:90 wt % and mixed by handshake. The reaction mixture was stirred at room temperature for 5 min, giving a liquid double salt ionic liquid ([$C_1$im-$SO_3$H][TFES])$_{10}$-(TFMSA)$_{90}$.

Example 2.1-II: Preparation of ([$C_1$im-$SO_3$H][TFES])$_{20}$-(TFMSA)$_{80}$ IL In a 40 mL glass tube, equipped with a stir bar, TFMSA (0.40 g) and ionic liquid [$C_1$im-$SO_3$H][TFES] (0.10 g) was added at 20:80 wt % and mixed by handshake. The reaction mixture was stirred at room temperature for 5 min, giving a liquid double salt ionic liquid ([$C_1$im-$SO_3$H][TFES])$_{20}$-(TFMSA)$_{80}$.

Example 2.1-III: Preparation of ([$C_1$im-$SO_3$H][TFES])$_{50}$-(TFMSA)$_{50}$ IL In a 40 mL glass tube, equipped with a stir bar, TFMSA (0.25 g) and ionic liquid [$C_1$im-$SO_3$H][TFES] (0.25 g) was added at 50:50 wt % and mixed by handshake. The reaction mixture was stirred at room temperature for 5 min, giving a liquid double salt ionic liquid ([$C_1$im-$SO_3$H][TFES])$_{50}$-(TFMSA)$_{50}$.

Example 2.2-I: Preparation of ([$C_1C_4$im][$HSO_4$])$_{10}$—($H_2SO_4$)$_{90}$ IL In a 40 mL glass tube, equipped with a stir bar, $H_2SO_4$ (0.45 g) and IL [$C_1C_4$im][$HSO_4$] (0.05 g, commercially available) was added at 10:90 wt % and mixed by handshake. The reaction mixture was stirred at room temperature for 5 min, giving a liquid double salt ionic liquid ([$C_1C_4$im][$HSO_4$])$_{10}$—($H_2SO_4$)$_{90}$.

Example 2.3-I: Preparation of ([$N_{111(16)}$][$HSO_4$])$_{10}$-(TFMSA)$_{90}$ IL In a 40 mL glass tube, equipped with a stir bar, TFMSA (0.45 g) and ionic liquid [$N_{111(16)}$][$HSO_4$] (0.05 g, commercially available) was added at 10:90 wt % and mixed by handshake. The reaction mixture was stirred at room temperature for 5 min, giving a liquid double salt ionic liquid ([$N_{111(16)}$][$HSO_4$])$_{10}$-(TFMSA)$_{90}$.

Example 3. Preparation of Ternary Mixtures of an Ionic Liquid, an Acid, and an Aromatic

Example 3.1-I: Preparation of ([$C_1$im-$SO_3$H][TFES])$_{10}$-(TFMSA)$_{90}$-(HMB)$_{10}$ Clathrate In a 40 mL glass tube, equipped with a stir bar, TFMSA (0.45 g) and ionic liquid [$C_1$im-$SO_3$H][TFES] (0.05 g) were added at 10:90 wt % and mixed by handshake. After a minute, 10 wt % of hexamethylbenzene (HMB; 0.05 g) was added and the reaction mixture was stirred at room temperature for 5 min, giving a liquid double salt ionic liquid clathrate ([$C_1$im-$SO_3$H][TFES])$_{10}$-(TFESA)$_{90}$-(HMB)$_{10}$.

Example 4. Acylation of Isobutylbenzene Reaction Apparatus and Procedure

Friedel-Crafts acylation of isobutylbenzene experiments were performed in a 20 mL glass reactor. The reaction mixture was analyzed offline by gas chromatography (GC), equipped with a flame ionization detector, and a DB-5 100 m column (J&W Scientific). Helium was used as the GC carrier gas and as the flame ionization detector (FID) makeup gas. The analysis conditions were: split ratio=50:1, injector temperature=280° C., detector temperature=300° C., carrier gas flow rate=20 sccm. The temperature program for GC analysis was as follows: initial column temperature 150° C./hold for 1 min, 10° C./min to 300° C./hold for 5 min.

All experiments were performed in batch. A typical experiment began with the addition of the catalyst into the 20 mL glass reactor equipped with a Teflon coated magnetic stir bar. The desired amount of isobutylbenzene and acetyl chloride were added into the reactor. The reaction mixture was stirred under desired reaction temperature and time. After a certain reaction time, stirring was stopped, and a small aliquot of mixture was withdrawn from the reaction mixture and monitored by using GC with FID. The results are shown in Table 2.

The results of Table 2 show that the use of the acid only (triflic acid) as well as the combination of the acid with the ionic liquid provide surprisingly high conversions and selectivities despite the fact that a catalyst:acetyl chloride mole ratio of about 0.26:1 was used. Conversions and selectivities would be expected to be about an order of magnitude lower using the same conditions, but replacing the catalysts of Table 2 with existing catalysts such as HF and $AlCl_3$.

TABLE 2

Alkylation of isobutylbenzene reaction results using catalysts.

| | Catalyst | Catalyst Amount (g) | T (° C.) | Time (h) | Conv. (%) | Product Sel. (%) |
|---|---|---|---|---|---|---|
| 1 | [$C_1$im-$SO_3$H][TFES] | 0.2 | 25 | 3 | Nil | Nil |
| 2 | ([$C_1$im-$SO_3$H][TFES])$_{10}$-(TFMSA)$_{90}$ | 0.5 | 25 | 3 | >99.9 | 96.1 |
| 3 | ([$C_1$im-$SO_3$H][TFES])$_{10}$-(TFMSA)$_{90}$ | 0.2 | 25 | 3 | 76.9 | 96.0 |

TABLE 2-continued

Alkylation of isobutylbenzene reaction results using catalysts.

| Catalyst | Catalyst Amount (g) | T (° C.) | Time (h) | Conv. (%) | Product Sel. (%) |
|---|---|---|---|---|---|
| 4 | 0.2 | 25 | 3 | 80.4 | 95.2 |
| 5 | 0.2 | 25 | 3 | 72.8 | 95.4 |
| | | Average | | 76.7 | 95.5 |
| | | Std dev | | 3.8 | 0.4 |
| 6 $([C_1im\text{-}SO_3H][TFES])_{20}\text{-}(TFMSA)_{80}$ | 0.2 | 25 | 3 | 62.1 | 95.9 |
| 7 $([C_1im\text{-}SO_3H][TFES])_{50}\text{-}(TFMSA)_{50}$ | 0.2 | 25 | 3 | 52.7 | 96.0 |
| 8 TFMSA | 0.2 | 25 | 3 | 74.7 | 95.3 |
| 9 | 0.2 | 25 | 3 | 72.3 | 95.3 |
| 10 | 0.2 | 25 | 3 | 67.6 | 95.6 |
| | | Average | | 71.5 | 95.4 |
| | | Std dev | | 3.6 | 0.2 |
| 11 $([C_1im\text{-}SO_3H][TFES])_{10}\text{-}(TFESA)_{90}\text{-}(HMB)_{10}$ | 0.2 | 25 | 3 | 60.8 | 95.2 |

Reaction condition: Catalyst (0.2 g), Isobutylbenzene (2.7 g; 20 mmol), acetyl chloride (0.4 g; 5 mmol), room temperature, 3 h.
Note:
TFMSA = Triflic acid; HMB = hexamethylbenzene.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

If not already included, all numeric values of parameters in the present disclosure are proceeded by the term "about" which means approximately. This encompasses those variations inherent to the measurement of the relevant parameter as understood by those of ordinary skill in the art. This also encompasses the exact value of the disclosed numeric value and values that round to the disclosed numeric value.

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the disclosure in various embodiments and with various modifications as suited to the particular use contemplated. It is intended that the scope of the disclosure be defined by the claims appended hereto and their equivalents.

What is claimed is:

1. A process for acylating an aromatic compound, the process comprising combining an aromatic compound, an acylating agent, and a catalyst composition under conditions to induce acylation of the aromatic compound with the acylating agent, the catalyst composition comprising components selected from the group consisting of (a) an ionic liquid, an acid, and an aromatic; and (b) an acid, a base capable of forming an ionic liquid with the acid, and an aromatic;

wherein the ionic liquid does not comprise a metal halide and the catalyst composition is free of a metal halide and the aromatic of the catalyst composition is not the aromatic compound being acylated.

2. The process of claim 1, wherein the ionic liquid does not comprise a non-metal halide and the catalyst composition is free of a non-metal halide.

3. The process of claim 1, wherein the aromatic of the catalyst composition is selected from an unsubstituted or substituted monocyclic aromatic.

4. The process of claim 1, wherein the aromatic of the catalyst composition has formula $C_6R_6$, wherein each R is independently selected from hydrogen, a halogen, and an unsubstituted or substituted alkyl group.

5. The process of claim 1, wherein the aromatic of the catalyst composition is selected from benzene, toluene, xylenes, mesitylene, hexamethylbenzene, and a halogenated benzene.

6. The process of claim 1, wherein the acid is triflic acid or tetrafluoroethane sulfonic acid.

7. The process of claim 1, wherein the ionic liquid comprises an imidazolium cation.

8. The process of claim 7, wherein the imidazolium cation has Formula B

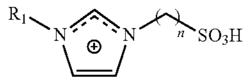

wherein $R_1$ is hydrogen or alkyl and n is 0, 3, 4, or 5.

9. The process of claim 8, wherein n is 0.

10. The process of claim 1, wherein the ionic liquid comprises $[HCF_2CF_2SO_3]^-$ as an anion.

11. The process of claim 1, wherein the ionic liquid comprises an imidazolium as a cation and $[HCF_2CF_2SO_3]^-$ as an anion.

12. The process of claim 1, wherein the aromatic compound of the catalyst composition is substituted, the acylating agent is an acyl halide, and the aromatic compound is acylated at its para position.

13. The process of claim 12, wherein the aromatic compound of the catalyst composition is isobutylbenzene and the acylating agent is acetyl chloride.

14. The process of claim 1, wherein a mole ratio of the catalyst composition to the acylating agent is no more than 0.5:1.

15. The process of claim 1, wherein the catalyst composition comprises components from (a).

16. The process of claim 15, wherein the catalyst composition is represented by $[IL]_x$-$[Acid]_{(100-x)}$-$[Aromatic]_y$, wherein x is (weight of the ionic liquid)/(combined weight of the ionic liquid and the acid)*100 and ranges from 5 weight % to 20 weight % and further wherein y is (weight of the aromatic of the catalyst composition)/(combined weight of the ionic liquid and the acid)*100 and ranges from 0.1 weight % to 25 weight %.

17. The process of claim 15, wherein the aromatic of the catalyst composition is selected from benzene, toluene, xylenes, mesitylene, hexamethylbenzene, and a halogenated benzene.

18. The process of claim 15, wherein the ionic liquid comprises an imidazolium as a cation and a sulfonate as an anion.

19. The process of claim 15, wherein the acid is a sulfonic acid.

20. The process of claim 16, wherein the aromatic of the catalyst composition is hexamethylbenzene; the ionic liquid is N-methyl, N-sulfonic acid imidazolium tetrafluoroethane sulfonate; and the acid is triflic acid or tetrafluoroethane sulfonic acid.

* * * * *